(12) United States Patent  
Li

(10) Patent No.: US 7,857,513 B2
(45) Date of Patent: Dec. 28, 2010

(54) TABLE APPARATUS IDENTIFYING METHOD AND MEDICAL IMAGING APPARATUS

(75) Inventor: Qinglei Li, Beijing (CN)

(73) Assignee: GE Medical Systems Global Technology Company, LLC, Waukesha, WI (US)

(*) Notice: Subject to any disclaimer, the term of this patent is extended or adjusted under 35 U.S.C. 154(b) by 915 days.

(21) Appl. No.: 11/734,521

(22) Filed: Apr. 12, 2007

(65) Prior Publication Data

US 2007/0251008 A1 Nov. 1, 2007

(30) Foreign Application Priority Data

Apr. 13, 2006 (CN) .................. 2006 1 0073611

(51) Int. Cl.
G01N 23/04 (2006.01)
H05G 1/02 (2006.01)
A61B 6/04 (2006.01)
G01D 18/00 (2006.01)

(52) U.S. Cl. .................. 378/209; 378/20; 378/63; 378/195; 378/207; 5/601

(58) Field of Classification Search ........... 378/20, 378/63, 195, 196, 205–207, 209; 5/601
See application file for complete search history.

(56) References Cited

U.S. PATENT DOCUMENTS

| 4,131,802 | A | * | 12/1978 | Braden et al. | 378/20 |
| 4,236,079 | A | * | 11/1980 | Sandland | 378/19 |
| 4,481,657 | A | | 11/1984 | Larsson | |
| 4,761,000 | A | | 8/1988 | Fisher et al. | |
| 5,013,018 | A | | 5/1991 | Sicek et al. | |
| 5,034,970 | A | * | 7/1991 | Yahata et al. | 378/20 |
| 5,113,420 | A | * | 5/1992 | Davis et al. | 378/20 |
| 5,541,856 | A | * | 7/1996 | Hammermeister | 378/196 |
| 6,045,262 | A | * | 4/2000 | Igeta et al. | 378/209 |
| 6,857,147 | B2 | | 2/2005 | Somasundaram | |
| 6,917,666 | B2 | * | 7/2005 | Wollenweber | 378/20 |
| 6,928,142 | B2 | * | 8/2005 | Shao et al. | 378/63 |
| 6,935,779 | B2 | * | 8/2005 | Zhang et al. | 378/207 |
| 6,935,780 | B2 | | 8/2005 | Barde et al. | |
| 7,000,271 | B2 | | 2/2006 | Varadharajulu | |
| 7,024,710 | B2 | | 4/2006 | Izuhara | |
| 7,165,885 | B2 | * | 1/2007 | Lumma | 378/193 |

(Continued)

FOREIGN PATENT DOCUMENTS

JP 2002330960 11/2002

*Primary Examiner*—Edward J Glick
*Assistant Examiner*—Thomas R Artman
(74) *Attorney, Agent, or Firm*—Armstrong Teasdale LLP

(57) ABSTRACT

To realize a method of automatically identifying a table apparatus and a medical imaging apparatus. There is provided a table apparatus identifying method in which when a table apparatus having a plurality of movable portions that are movable in the respective axial directions, independently, an absolute position of each of the movable portions on the axis is detected with respect to each of the axes, the passages of the movable portion at the predetermined two positions apart from each other by the given distance along the axis are optically detected, the respective absolute positions of the movable portion at that time is stored as characterization information, and the arrivals of the movable portion at two block positions on both ends of the axis are detected, respectively, and the respective absolute positions of the movable portion at that time are stored as the configuration information.

20 Claims, 11 Drawing Sheets

U.S. PATENT DOCUMENTS 7,186,024 B2 3/2007 Varadharajulu
7,192,188 B2 * 3/2007 Maschke .................... 378/197
7,382,851 B2 * 6/2008 Inoue et al. .................... 378/4
7,639,782 B2 * 12/2009 Zelnik et al. .................. 378/62

* cited by examiner

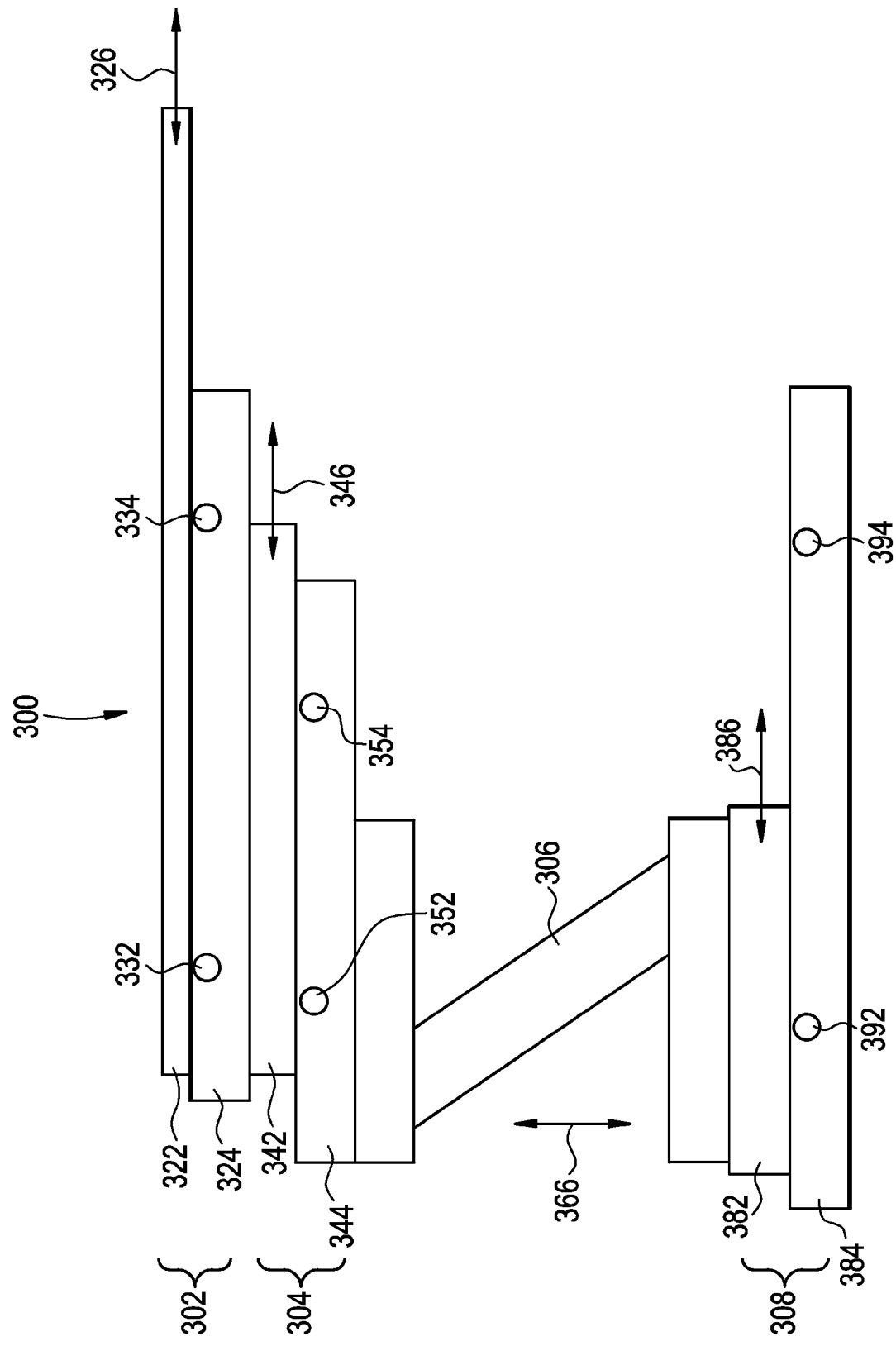

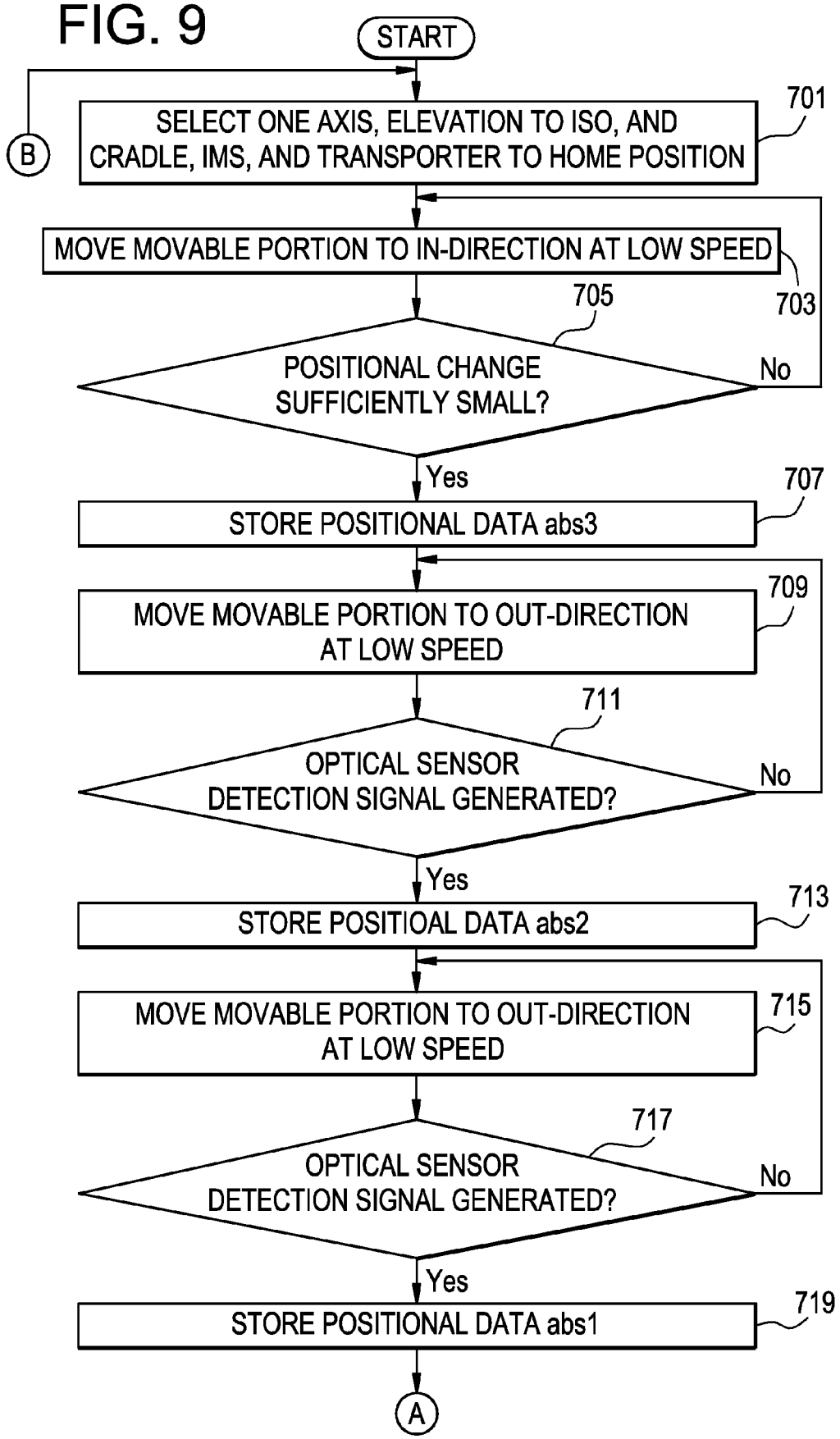

TABLE APPARATUS IDENTIFYING METHOD AND MEDICAL IMAGING APPARATUS

CROSS REFERENCE TO RELATED APPLICATIONS

This application claims the benefit of Chinese Patent Application No. 200610073611.4 filed Apr. 13, 2006.

BACKGROUND OF THE INVENTION

The present invention relates to a table apparatus identifying method and a medical imaging apparatus, and more particularly to a method of identifying a table apparatus having a plurality of movable portions that are movable in the respective axial directions, respectively, and a medical imaging apparatus having the table apparatus.

In a PET-CT device that combines a PET (position emission tomography) device with an X ray CT (computed tomography) device together, there is used a table apparatus having a plurality of movable portions that are movable, independently (for example, refer to Patent Document 1).

As the plurality of movable portions, for example, there are a cradle that supports and moves an object to be detected in a horizontal direction, an intermediate support: IMS that supports and moves the cradle in the horizontal direction, an elevation that supports and moves the IMS in a vertical direction, and a transporter that supports and moves the elevation in the horizontal direction.

In the table apparatus, the apparatus is identified before operation. The apparatus is identified by confirmation of the characterization and the configuration of the apparatus.

The characterization is conducted by correcting a measured value of a distance measurement system in the movable portions of the respective axes. The measured value is corrected in such a manner that pins are manually inserted into holes that are defined in predetermined two positions along the movement axis, respectively, the outputs of an encoder when the movement of the movable portions is blocked by those pins are read, respectively, and the correction is conducted by using those read values and a distance between those pin holes which is known in advance.

The configuration is confirmed by electrically reading the type of the configuration pins that are inserted into an interface board. The configuration pins are prepared for each type of the configurations, and an appropriate pin is inserted into the interface board.

[PATENT DOCUMENT 1] JP 2002-330960

The table apparatus using the above method takes time and labor since manual works are required. Moreover, the reliability of the apparatus identification depends on the skill of a worker.

SUMMARY OF THE INVENTION

Therefore, an object of the present invention is to realize a method of automatically identifying a table apparatus and a medical imaging apparatus.

In order to solve the above object, according to a first aspect of the present invention, there is provided a table apparatus identifying method in which when a table apparatus having a plurality of movable portions that are movable in the respective axial directions, independently, an absolute position of each of the movable portions on the axis is detected with respect to each of the axes, the passages of the movable portion at the predetermined two positions apart from each other by the given distance along the axis are optically detected, the respective absolute positions of the movable portion at that time is stored as characterization information, and the arrivals of the movable portion at two block positions on both ends of the axis are detected, respectively, and the respective absolute positions of the movable portion at that time are stored as the configuration information.

According to a second aspect of the present invention, there is provided a medical imaging apparatus, comprising: a first data collection unit that collects projection data attributable to radiations generated by a medicinal drug given to an object to be detected; a second data collection unit that scans the object to be detected with X-rays to collect the projection data; an image reconstruction unit that reconstructs images on the basis of the projection data that has been collected by the first data collection unit and the second data collection unit, respectively; a table apparatus that has a plurality of movable portions movable in the respective axes, independently, and selectively transports the object to be detected to a data collection position of the first data collection unit or a data collection position of the second data collection unit; and a table apparatus identifying unit that identifies the table apparatus, wherein the table apparatus identifying unit includes absolute position detecting means for detecting absolute positions of the movable portions on the axes, first detecting means for optically detecting the passages of the movable portions at two given positions apart from each other by a given distance in the respective axes of the table apparatus, first memory means for storing the respective absolute positions of the movable portions when the first detecting means detects the passages of the movable portions as characterization information, second detecting means for detecting the arrivals of the movable portions at two block positions on both ends of the axes, and second memory means for storing the respective absolute positions of the movable portions when the second detecting means detects the arrivals of the movable portions as the configuration information.

It is preferable that optical sensors that are disposed at the respective positions detect the passages of the movable portions at the two positions because of noncontact detection.

It is preferable that the optical sensors are light receiving sensors because of a light receiving type.

It is preferable that the optical sensors are light shielding sensors because of a light shielding type.

It is preferable that a flag is set after the characterization information and the configuration information are stored with respect to all of the axes because it is defined whether the table apparatus is identified, or not.

It is preferable that whether the identification of the table apparatus is necessary, or not, is determined on the basis of the presence or absence of the flag because the duplication of the table apparatus identification is prevented.

It is preferable that the configuration of the table apparatus is displayed on a user interface on the basis of the configuration information.

According to the invention from the above respective viewpoints, in each of the axes, an absolute position of the movable portion on the axis is detected, the passages of the movable portion at the predetermined two positions apart from each other by the given distance along the axis are optically detected, and the respective absolute positions of the movable portion at that time is stored as characterization information. Also, the arrivals of the movable portion at two block positions on both ends of the axis are detected, respectively, and the respective absolute positions of the movable portion at that time are stored as the configuration information. As a result, the table apparatus can be automatically identified.

Further objects and advantages of the present invention will be apparent from the following description of the preferred embodiments of the invention as illustrated in the accompanying drawings.

BRIEF DESCRIPTION OF THE DRAWINGS

FIG. 6 is a diagram showing the structure of a table apparatus.

FIG. 9 is a flowchart showing a process for identifying a table apparatus.

DETAILED DESCRIPTION OF THE INVENTION

Figure 1:
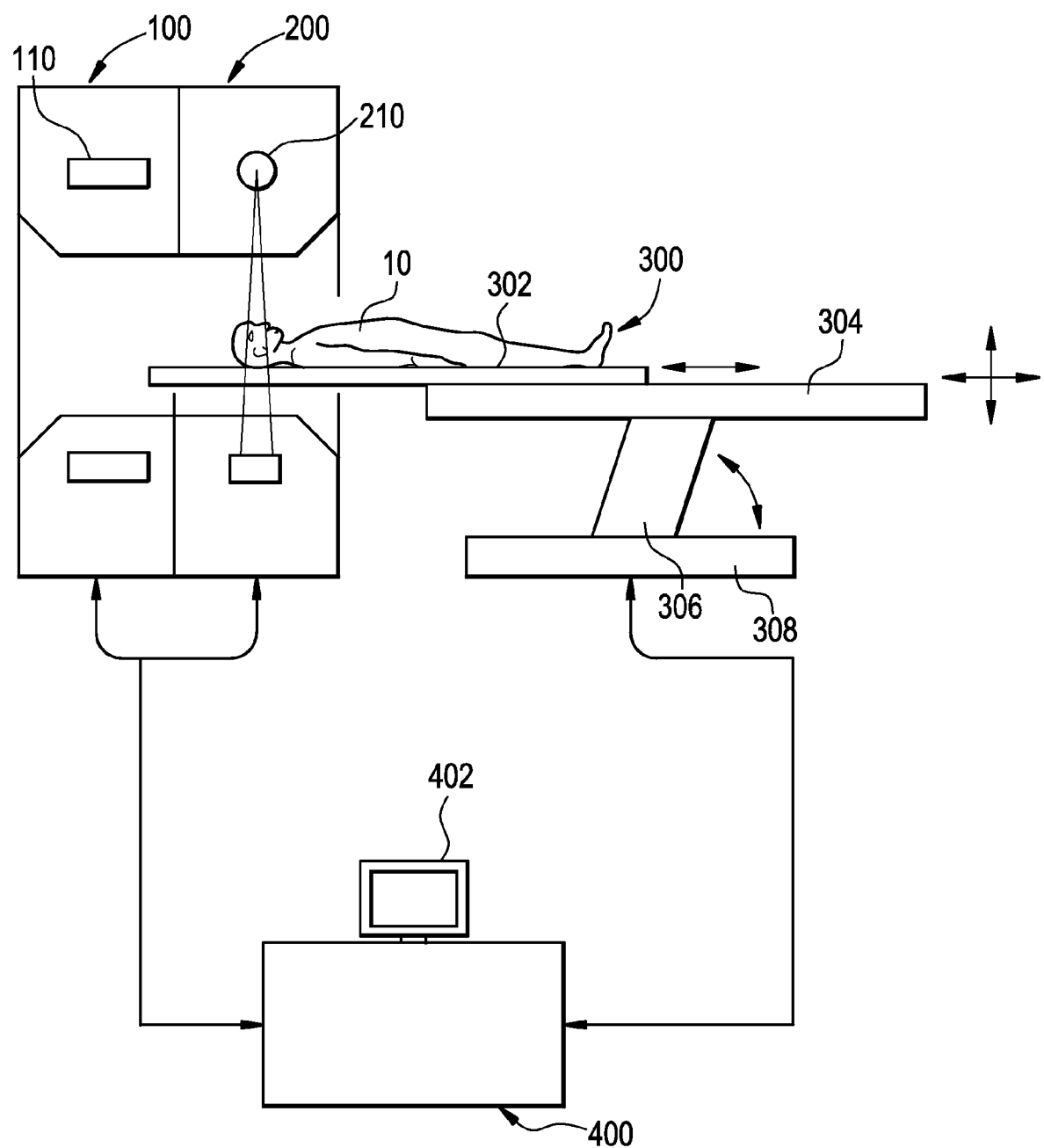
FIG. 1 is a diagram showing the structure of a PET-CT device according to an example of the best mode for carrying out the present invention.

Hereinafter, a description will be given of the best modes for carrying out the present invention with reference to the attached drawings. The present invention is not limited to the best modes for carrying out the present invention. FIG. 1 shows a schematic structure of a PET-CT device. This device is an example of the best mode for carrying out the present invention. The structure of this device shows an example of the best mode for carrying out the present invention related to a medical imaging apparatus. The operation of this device shows an example of the best mode for carrying out the present invention related to a table apparatus identifying method.

This device has a PET gantry 100, a CT gantry 200, a table apparatus 300, and an operator console 400. The PET gantry 100 detects radiations that are generated by an object to be detected 10 which is carried in by the table apparatus 300 through a radiation detection unit 110. Then, the PET gantry 100 collects projection data attributable to the radiations, and inputs the projection data to the operator console 400. A medicinal drug for generation of radiations is given the object to be detected 10 in advance. The PET gantry 100 is an example of a first data collection unit according to the present invention.

The CT gantry 200 scans the object to be detected 10 which is carried in by the table apparatus 300 with an X-ray irradiation/detection unit 210, collects the projection data attributable to X-rays, and then inputs the projection data to the operator console 400. The CT gantry 200 is an example of a second data collection unit according to the present invention.

The operator console 400 conducts image reconstructions on the basis of the projection data inputted from the PET gantry 100 and the CT gantry 200 by a computer incorporated into the operator console 400, respectively. Then, the operator console 400 displays the reconstructed images on a display 402. The operator console 400 is an example of an image reconstruction unit according to the present invention.

The operator console 400 controls the PET gantry 100, the CT gantry 200, and the table apparatus 300. Under the control by the operator console 400, the PET gantry 100 and the CT gantry 200 conduct a data collection, respectively, and the table apparatus 300 conducts the positioning of the object to be detected 10 so that the data collection is conducted with respect to given portions. The table apparatus 300 is an example of the table apparatus according to the present invention.

The positioning is conducted by adjusting a horizontal movement distance of a cradle 302 as well as the height of a table top 304 that supports the cradle 302. The height adjustment of the table top 304 is conducted by swinging a column 306 centering on an attached portion of a base 308 onto the column 306.

Figure 2:
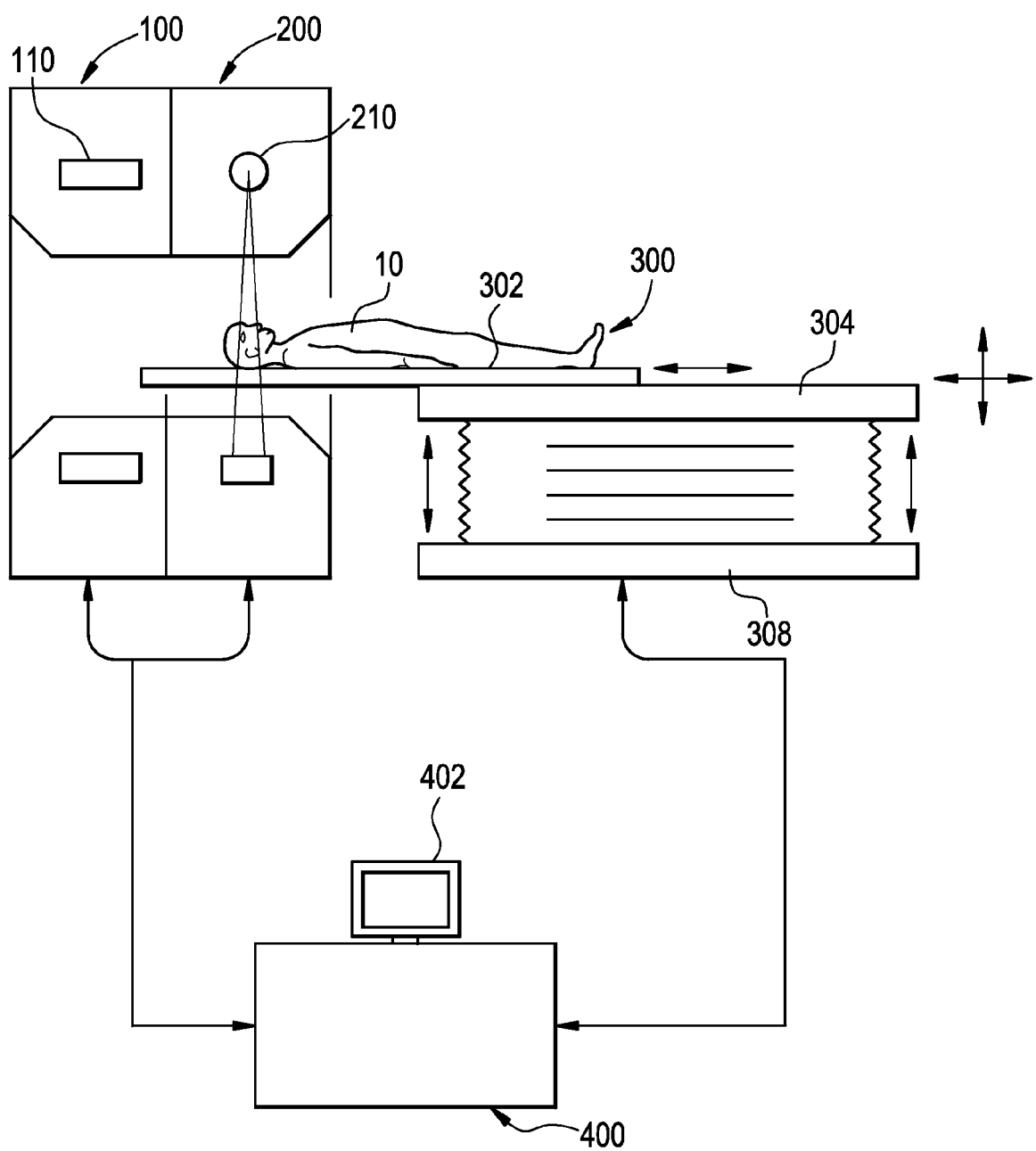
FIG. 2 is a diagram showing the structure of a PET-CT device according to an example of the best mode for carrying out the present invention.

As shown in FIG. 2, the table apparatus 300 may be of a system in which the table top 304 moves up and down vertically with respect to the base 308. The table top 304 is moved up and down by an elevator mechanism incorporated into the table top 304.

Figure 3:
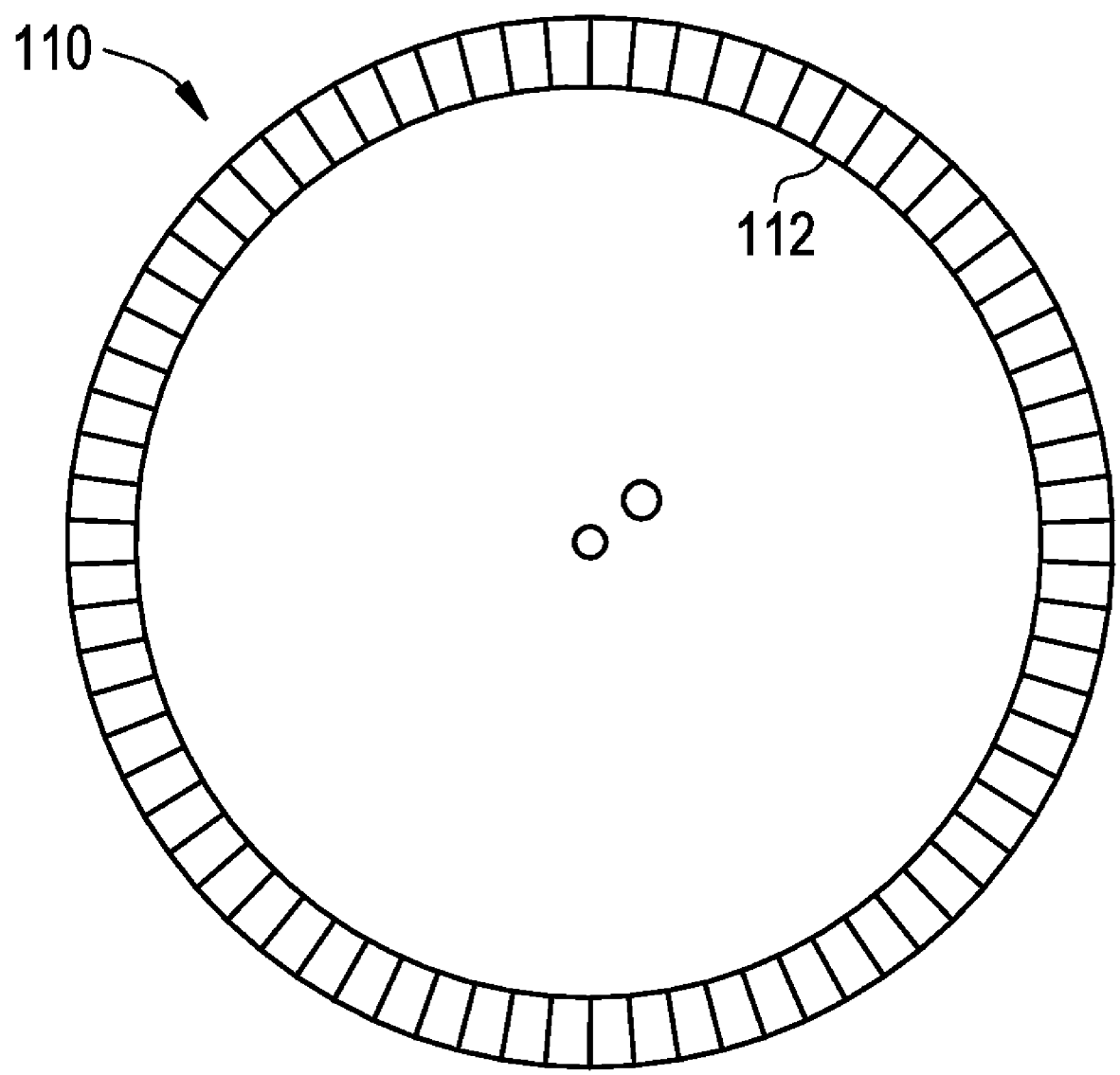
FIG. 3 is a diagram showing the structure of a radiation detection unit.

FIG. 3 schematically shows the structure of the radiation detection unit 1 10. As shown in FIG. 3, the radiation detection unit 110 has a plurality of detection cells 112 that are so arranged as to form an annular ring or a circular cylinder which is concentric with a photograph center O. The radiation detection unit 110 detects the radiation by the individual detection cells 112, respectively.

Figure 4:
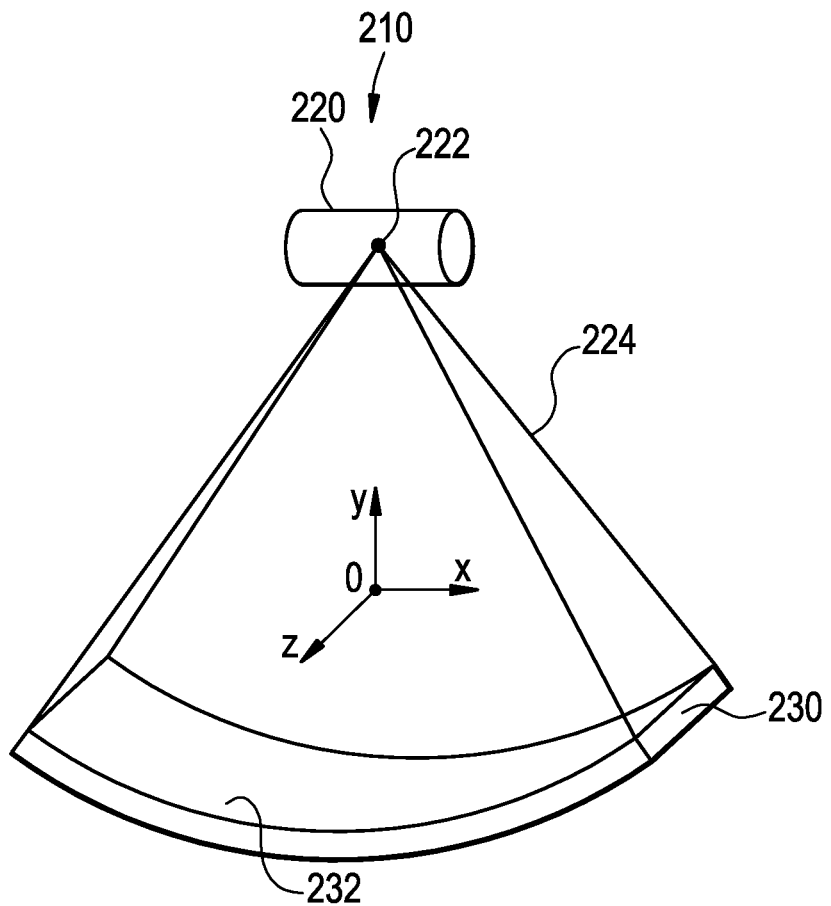
FIG. 4 is a diagram showing the structure of an X-ray irradiation/detection unit.

FIG. 4 schematically shows the structure of the X-ray irradiation/detection unit 21 0. The X-ray irradiation/detection unit 210 is so designed as to detect X-rays 224 that are radiated from a focal point 222 of an X-ray tube 220 by an X-ray detector 230.

The X-rays 224 are X-rays of a cone beam or a fan beam which is generated by a collimator not shown. The X-ray detector 230 has an X-ray incident plane 232 that broadens two-dimensionally in correspondence with the spread of X-rays. The X-ray incident plane 232 is so curved as to constitute a part of the cylinder. The center axis of the cylinder passes through the focal point 222.

The X-ray irradiation/detection unit 210 rotates about the center axis that passes through the photograph center O. The center axis is in parallel with the center axis of the partial cylinder that is formed by the X-ray detector 230. The direction of the center axis of rotation is a Z direction, a direction that connects the photograph center O and the focal point 222 is a Y direction, and a direction perpendicular to the Z direction and Y direction are an X direction. Those X, Y, and Z axes are three axes of a rotating coordinate system having the Z axis as the center axis.

Figure 5:
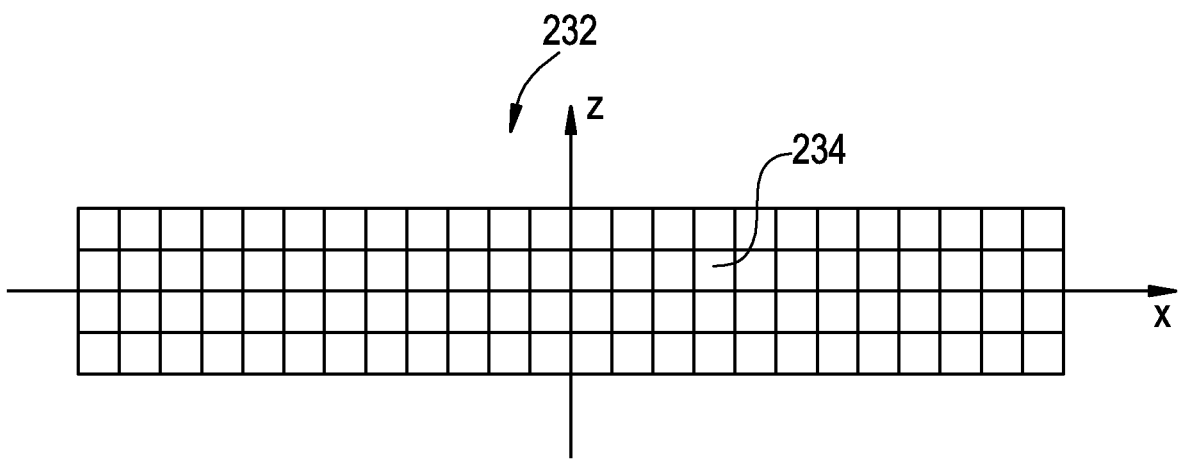
FIG. 5 is a diagram showing the structure of an X-ray incident plane of the X-ray detector.

FIG. 5 shows a schematic plan view of the X-ray incident plane 232 of the X-ray detector 230. The X-ray incident plane 232 has the detection cells 234 arranged in the X-direction and the Z-direction, two-dimensionally. In other words, the X-ray incident plane 232 is a two-dimensional array of the detection cells 234. In the case of using the fan beam X-rays, the X-ray incident plane 232 may be a one-dimensional array of the detection cells 234.

FIG. 6 schematically shows the structure of the table apparatus 300 in more detail. As shown in FIG. 6, the cradle 302 is made up of a movable plate 322 and a support 324. The object to be detected is put on the movable plate 322, and the movable plate 322 can be retreated on the support 324 in the horizontal direction as indicted by an arrow 326. The movable plate 322 is an example of the movable portions according to the present invention. The arrow 326 expresses one of the plural axes of the table apparatus 300.

In this example, the rightward direction of the arrow is an in-direction, and the leftward direction of the arrow is an out-direction. The in-direction is a direction toward which the object to be detected is carried in with respect to the PET gantry 100 or the CT gantry 200, and the out direction is a direction toward which the object to be detected is carried out.

The support 324 has a driving mechanism for moving the movable plate 322 incorporated therein. The support 324 also has a detector for detecting the absolute positions of the movable plates 322 on the support 324 incorporated therein. The detector of this type is, for example, an encoder. The encoder is an example of the absolute position detecting means according to the present invention.

The support 324 further includes two optical sensors 332 and 334. Those two optical sensors 332 and 334 are arranged at a given interval along the movement axis of the movable plate 322. The optical sensors 332 and 334 are an example of the first detecting means according to the present invention. The optical sensors 332 and 334 will be further described later.

The support 324 further has stoppers for the movable plate 322 incorporated therein. The stoppers are disposed at both ends of the support 324, respectively, and define the maximum arrival positions of the movable plate 322 in the in-direction and the out-direction.

The cradle 302 is supported by the table top 304. The table top 304 is made up of the movable plate 342 and the support 344. The movable plate 342 can be retreated on the support 344 horizontally as indicated by an arrow 346 while the cradle 302 is put on the movable plate 342. The support 324 of the cradle 302 is fixed by the movable plate 342. The movable plate 342 is an example of the movable portion according to the present invention. The arrow 346 expresses one of the plural axes of the table apparatus 300. In this example, the rightward direction is an in-direction, and the leftward direction is an out-direction.

The support 344 has a driving mechanism for moving the movable plate 342 incorporated therein. The support 344 also has a detector for detecting the absolute position of the movable plate 342 on the support 344 incorporated therein. The detector of this type is, for example, an encoder. The encoder is an example of the absolute position detecting means according to the present invention.

The support 344 further has two optical sensors 352 and 354. Those two optical sensors 352 and 354 are arranged along the movement axis of the movable plate 342 at a given distance. The optical sensors 352 and 354 are an example of the first detecting means according to the present invention. A description will be further given of the optical sensors 352 and 354 later.

The support 344 further has stoppers for the movable plate 342 incorporated therein. The stoppers are disposed at both ends of the support 344, respectively, so as to define the maximum arrival positions of the movable plate 342 in the in-direction and the out-direction. Hereinafter, the table top 304 will be also called "inter mediate support (IMS)".

The table top 304 is supported by the column 306. The support 344 of the table top 304 is fixed to a top of the column 306. The table top 304 moves up and down vertically by swing of the column 306 as indicated by an arrow 366. An angle of the column 306 is detected by a potentiometer, and the angle is converted into the height of the table top 304. The arrow 366 expresses one of the plural axes of the table apparatus 300. Hereinafter, the column 306 will be also called "elevation". The elevation may be expanded and contracted vertically as shown in FIG. 2.

The column 306 is supported by a base 308. The base 308 is made up of a movable plate 382 and a support 384. The movable plate 382 can be retreated on the support 384 horizontally as indicated by an arrow 386 in a state where the column 306 is put on the movable plate 382. The base of the column 306 is fixed onto the movable plate 382. The movable plate 382 is an example of the movable portion according to the present invention. An arrow 386 expresses one of the plural axes of the table apparatus 300. In this example, the rightward direction is an in-direction, and the leftward direction is an out-direction.

The support 384 has a driving mechanism for moving the movable plate 382 incorporated therein. The support 384 also has a detector for detecting the absolute position of the movable plate 382 on the support 384 incorporated therein. The detector of this type is, for example, an encoder. The encoder is an example of the absolute position detecting means according to the present invention.

The support 384 further includes two optical sensors 392 and 394. Those two optical sensors 392 and 394 are arranged at a given interval along the movement axis of the movable plate 382. The optical sensors 392 and 394 are an example of the first detecting means according to the present invention. The optical sensors 392 and 394 will be further described later.

The support 384 has stoppers for the movable plate 382 incorporated therein. The stoppers are disposed at both ends of the support 384, respectively, so as to define the maximum arrival positions of the movable plate 382 in the in-direction and the out-direction. Hereinafter, the base 308 will be called "transporter".

The transporter 308 retreats a structure from the elevation 306 up horizontally. The elevation 306 moves up and down the structure from the IMS 304 up vertically. The IMS 304 retreats the entire cradle 302 horizontally. The cradle 302 retreats the movable plate 322 horizontally.

The three-step horizontal movement of the mechanism consisting of the transporter 308, the IMS 304, and the cradle 302 increases a total movable range of the movable plate 322. For that reason, it is possible to seamlessly image the object to be detected from the vertex to the feet by any one of the PET gantry 100 and the CT gantry 200.

It is possible that the movement of the IMS 304 or (and) the transporter 308 is conducted by two or more steps, and the horizontal movement of four or more steps is conducted. Alternatively, it is possible that the IMS 304 or (and) the transporter 308 is omitted, and the horizontal movement is conducted by two or less step. Hereinafter, an example in which the horizontal movement is conducted by three steps will be described. However, the same is applied to a case in which the horizontal movement is conducted by four or more steps, or two or less steps.

Figure 7A:
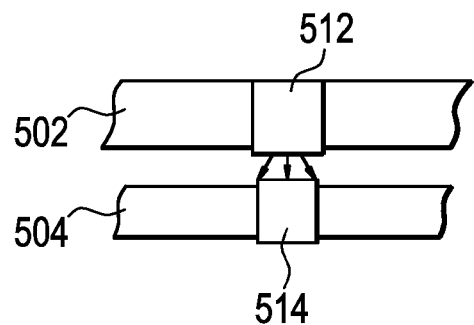
FIGS. 7a and 7b are diagrams showing an optical sensor structure.
Figure 7B:
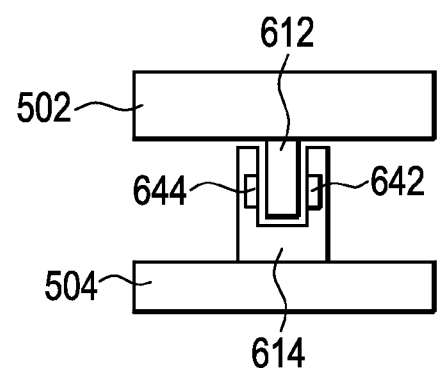

FIGS. 7 show a structural example of the optical sensor 332. The same is applied to the optical sensors 334, 352, 354, 392, and 394. FIG. 7A is a light receiving type sensor, and FIG. 7(b) is a light shielding type sensor. Those optical sensors are examples of the optical sensors according to the present invention, respectively. The light receiving type sensor is an example of the light receiving type sensor according to the present invention. The light shielding type sensor is an example of the light shielding type sensor according to the present invention.

The light receiving type sensor shown in FIG. 7(a) is structured in such a manner that a light emitting element 512 and a light receiving element 514 are disposed on one and another of two objects 502 and 504 that relatively move, respectively. One object 502 is, for example, the movable plates 322, 342, and 382, and another object 504 is, for example, the supports 324, 344, and 384. The light emitting element 512 and the light receiving element 514 may be mutually replaced with each other.

The light of the light emitting element 512 is inputted to the light receiving element 514 only when the light emitting element 512 rightly face each other. This phenomenon makes it possible to detect whether those two objects 502 and 504 satisfy a specific positional relationship, or not.

The light shielding type sensor shown in FIG. 7(b) is structured in such a manner that a light shielding element 612 and a slot element 614 are disposed on one and another of two objects 502 and 504 that relatively move, respectively. One object 502 is, for example, the movable plates 322, 342, and 382, and another object 504 is, for example, the supports 324, 344, and 384. The light shielding element 612 and the slot element 614 may be mutually replaced with each other.

The light shielding element 612 passes through a slot of the slot element 614 with the relative movement of those two objects 502 and 504. A direction of the relative movement of the two objects 502 and 504 is perpendicular to a paper surface. The slot element 614 has a light emitting element 642 and a light receiving element 644 which oppose to each other with the interpolation of the slot.

The light of the light emitting element 642 which is inputted to the light receiving element 644 is shielded only when the light shielding element 612 enters the slot of the slot element 614. This phenomenon makes it possible to detect whether the two objects 502 and 504 satisfy a specific positional relation, or not.

The use of the optical sensor makes it possible to detect whether the two objects 502 and 504 satisfy a specific positional relation, or not, in a noncontact manner. When the optical sensor is the light receiving type sensor, detection can be conducted by the light receiving system, and when the optical sensor is the light shielding type sensor, detection can be conducted by the light shielding system.

In the light receiving type sensor, only one light emitting element 512 or light receiving element 514 is disposed on any one of the two objects 502 and 504, and two other light emitting elements 512 or light receiving elements 514 are disposed on the other object 502 or 504.

In other words, when one light emitting element 512 is disposed on the object 502, two light receiving elements 514 are disposed on the object 504. When two light emitting elements 512 are disposed on the object 502, one light receiving element 514 is disposed on the object 504.

When one light emitting element 512 is disposed on the object 504, two light receiving elements 514 are disposed on the object 502. When two light emitting elements 512 are disposed on the object 504, one light receiving element 514 is disposed on the object 502. Regardless of the light emitting elements or the light receiving elements, an interval between two elements is a predetermined constant interval.

In the light shielding type sensor, only one light shielding element 612 or slot element 614 is disposed on any one of the two objects 502 and 504, and two other light shielding elements 612 or slot elements 614 are disposed on the other object 502 or 504.

In other words, when one light shielding element 612 is disposed on the object 502, two slot elements 614 are disposed on the object 504. When two light shielding elements 612 are disposed on the object 502, one slot element 614 is disposed on the object 504.

When one light shielding element 612 is disposed on the object 504, two slot elements 614 are disposed on the object 502. When two light shielding elements 612 are disposed on the object 504, one slot element 614 is disposed on the object 502. Regardless of the light shielding elements or the slot elements, an interval between two elements is a predetermined constant interval.

The use of the above optical sensor makes it possible to detect the passages of the movable plates 322, 342, and 382 at the two positions which are set along the respective axes in advance, respectively. Then, encode signals at that time are stored, thereby making it possible to obtain the positional data of the movable plates 322, 342, and 382 at the two positions, respectively.

Figure 8A:
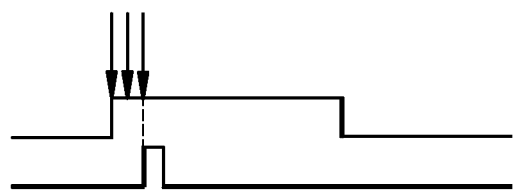
FIGS. 8a and 8b are diagrams showing a timing at which positional data is obtained.
Figure 8B:
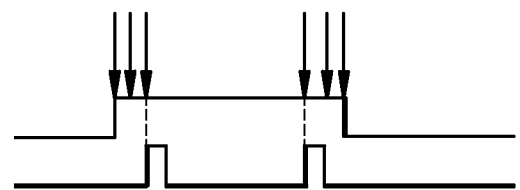

In this situation, in order to enhance a precision in the positional data, for example, as shown in FIG. 8(a), the encode signal when the detection signals are stable over plural samplings may be stored. Alternatively, as shown in FIG. 8(b), there may be obtained an average value of the stored value when the detection signals are stable over several samplings after the detection signals rise, and the stored value when the detection signals are stable over several samplings before the detection signals fall.

Figure 10:
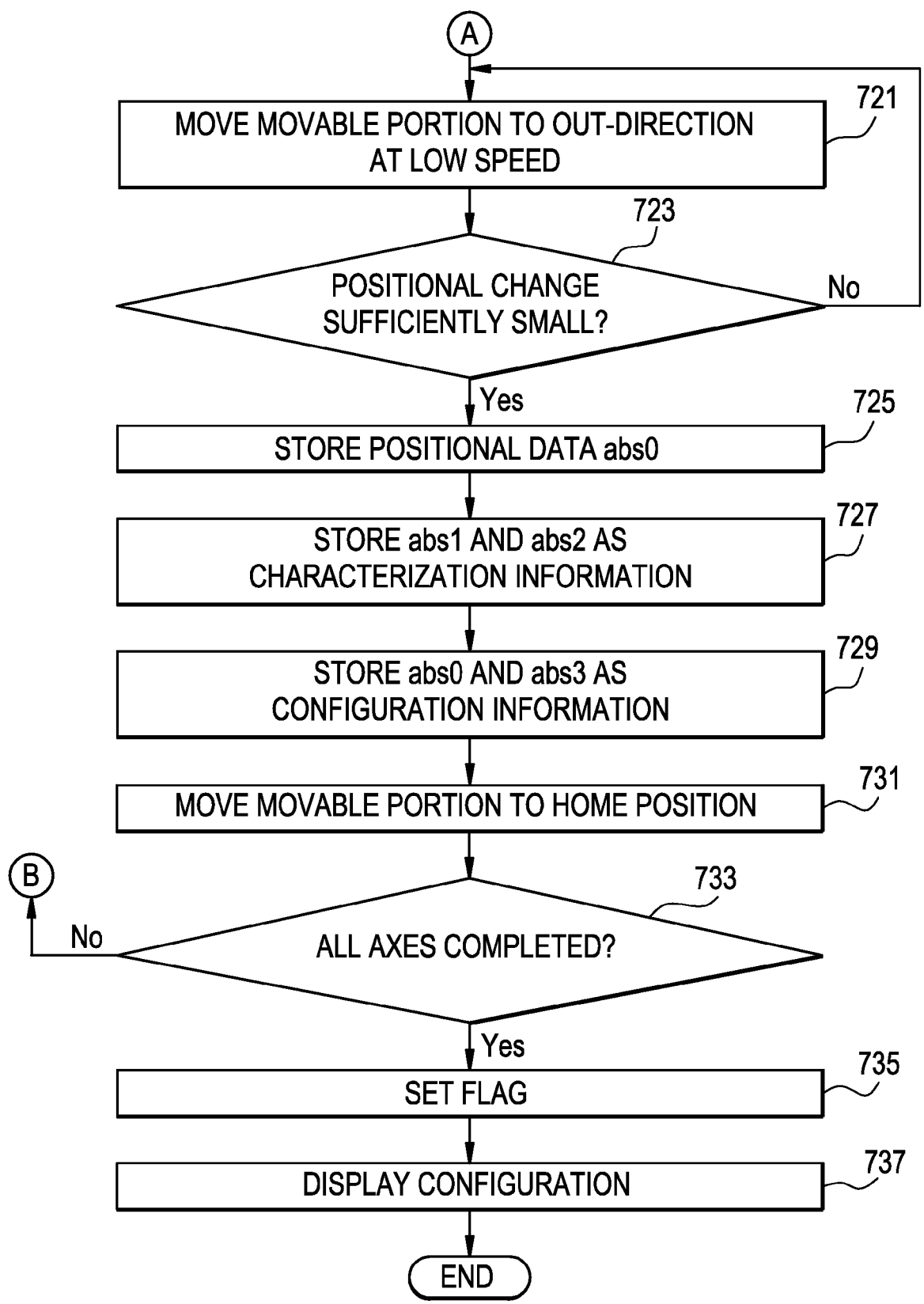
FIG. 10 is a flowchart showing a subsequent process for identifying the table apparatus.

A description will be given of a process of identifying the table apparatus 300 of the above type. FIGS. 9 and 10 show flowcharts of the process. This process is automatically implemented under the control by the operator console 400. The operator console 400 controls the process by means of a table control firmware, a TGP (table gantry board) firmware, or a host computer. The operator console 400 is an example of the table apparatus identifying device according to the present invention.

When the process starts according to a command from the operator or the host computer, one axis is selected, and the elevation is set to a height corresponding to the ISO (isocenter), and the cradle, the IMS, and the transporter are moved to a home position, in Step S701. One axis that is first selected is, for example, a cradle.

In Step S703, the movable portion is moved in the in-direction at a low speed. With the above operation, for example, the cradle 302 is moved in the in-direction at a low speed.

In Step S705, it is determined whether the positional change of the movable portion is sufficiently small, or not. When the positional change of the movable portion is not sufficiently small, the control is returned to Step S703, to thereby continue a low-speed movement of the movable portion in the in-direction. When the positional change of the movable portion is not sufficiently small, the operation of Steps 703 and 705 is repeated.

When the movable portion abuts against the stopper in the in-direction, the movement of the movable portion is blocked. In this situation, since the positional change of the movable portion is sufficiently small, this fact is determined in Step S705, and the positional data abs 3 of the movable portion in that situation is stored in Step S707. The determination in Step S705 is conducted by a computer within the operator console 400. The computer is an example of second detecting means according to the present invention.

Then, the movable portion is moved at a low speed in the out-direction in Step S709, and it is determined whether the detection signal of the optical sensor has been generated, or not, in Step S711. When it is determined that the detection signal of the optical sensor has not been generated, the control is returned to Step S709, and the movement of the movable portion in the out-direction continues. The operation of Steps S709 and S711 is repeated while the detection signal of the optical sensor is not generated.

During a process of moving the movable portion in the out-direction, the movable portion passes through a position at which the optical sensor at the in-side (for example, the optical sensor 334) in the two optical sensors is located. In this situation, since the detection signal of the optical sensor is generated, this fact is determined in Step S711. Under the above circumstances, the positional data abs 2 of the movable portion is stored in this situation in Step S713, and the movement of the movable portion in the out-direction continues.

In Step S717, it is determined whether the detection signal of the optical sensor has been generated, or not. When it is determined that the detection signal of the optical sensor has not been generated, the control is returned to Step S715, and the movement of the movable portion in the out-direction continues. The operation of Steps S715 and S717 is repeated while the detection signal of the optical sensor is not generated.

During a process of moving the movable portion in the out-direction, the movable portion passes through a position at which the optical sensor at the out-side (for example, the optical sensor 332) in the two optical sensors is located. In this situation, since the detection signal of the optical sensor is generated, this fact is determined in Step S711. Under the above circumstances, the positional data abs 1 of the movable portion is stored in this situation in Step S719, and the movement of the movable portion in the out-direction continues.

It is determined whether the positional change of the movable portion is sufficiently small, or not, in Step S723. When the positional change of the movable portion is not sufficiently small, the control is returned to Step S721, and the low-speed movement of the movable portion in the out-direction continues. The operation of Steps S721 and S723 is repeated while the positional change of the movable portion is not sufficiently small.

When the movable portion abuts against the stopper in the out-direction, the movement of the movable portion is blocked. In this situation, since the positional change of the movable portion is sufficiently small, this fact is determined in Step S723, and the positional data abs 0 of the movable portion in that situation is stored in Step S725. The determination in Step S723 is conducted by a computer within the operator console 400. The computer is an example of the second detecting means according to the present invention.

The movable portion positions abs 1 and abs 2 among the movable portion positions abs 0, abs 1, abs 2, and abs 3 thus obtained are stored as the characterization information in Step S727, and the movable portion positions abs and abs 3 are stored as the configuration information in Step S729. Then, the movable portion is returned to a home position in Step S731. With this operation, the acquisition of the characterization information and the configuration information with respect to one axis is finished.

The characterization information is stored in an appropriate memory medium such as a flash memory. The memory medium of this type is an example of the first memory means according to the present invention. The configuration information is stored in an appropriate memory medium such as a flash memory. The memory medium of this type is an example of the second memory means according to the present invention.

It is determined whether the above process has been completed with respect to all of the axes, or not, in Step S733, and when the above process has not yet been completed with respect to all of the axes, the control is returned to Step S701. Then, the same processing as above is conducted on the second axis (for example, IMS) in the operation after Step S701, and the characterization information and the configuration information which are related to that axis are stored. The characterization information and the configuration information are stored in the same manner with respect to the transporter.

Figure 11:
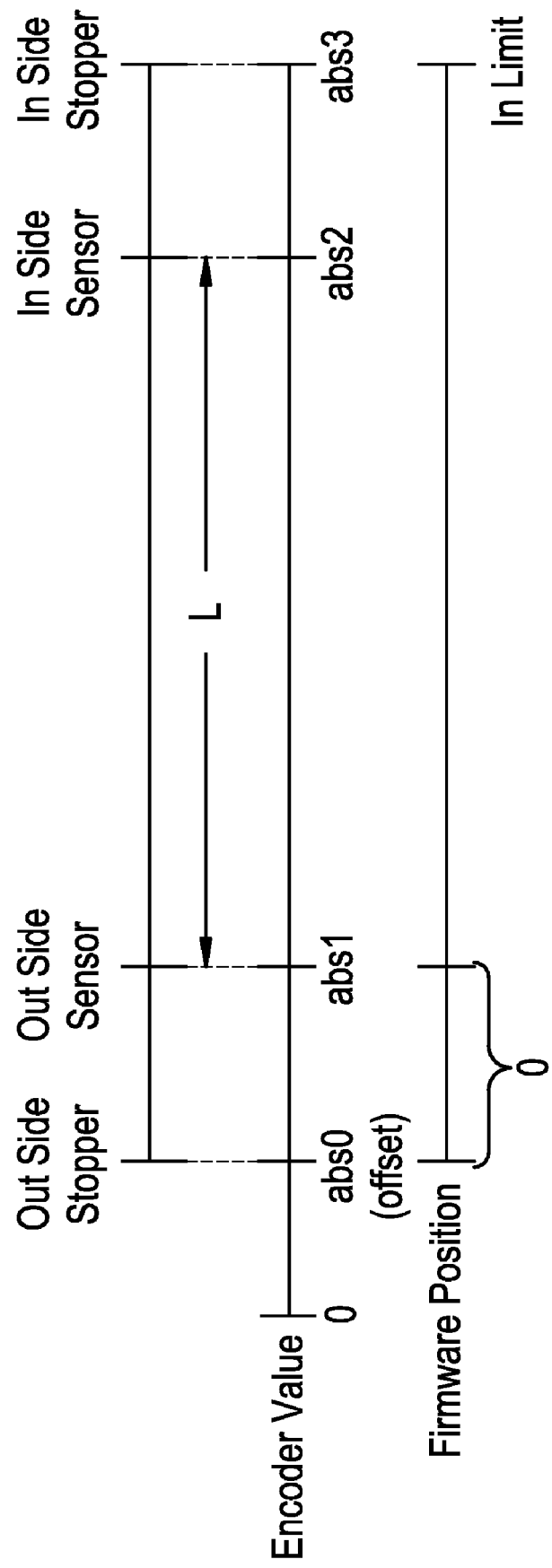
FIG. 11 is a diagram showing a relationship of an encoder value and a firmware position.

FIG. 11 shows a relationship of the movable portion positions abs 0, abs 1, abs 2, and abs 3. Those positions express hardware positions of an encoder, that is, encoder values. Since the position 0 of the encoder is outside of the out-side stopper, the encoder value has an offset.

The gain value of the encoder is obtained by using the characterization information abs 1 and abs 2 by the following expression.

$$\text{Gain\_value} = L/(\text{abs2} - \text{abs1}) \quad (1)$$

In this example, L is a distance between the two optical sensors, and a predetermined known value. The unit of the distance L is, for example, mm.

The gain value calculation of the expression (1) is the contents of the characterization. The characterization is conducted on the cradle, the IMS, and the transporter, respectively.

The position of the movable portion with reference to the out-side stopper is obtained by using the gain value by the following expression.

$$\text{Position} = \text{Gain\_value} \neq (\text{encoder\_value} - \text{abs0}) \quad (2)$$

The unit of the position of the movable portion is, for example, mm. That the movement distance of the movable portion from the out-side stopper to the in-side stopper is calculated by the expression (2) is the contents of the configuration confirmation. The configuration confirmation is conducted on the cradle, the IMS, and the transporter, respectively.

The configuration confirmation of the elevation is conducted by converting the output value of the potentiometer when the movable portion moves to the lowest position and the output value of the potentiometer when the movable portion moves to the highest position into the heights, respectively.

The position of the movable portion with reference to the firmware position, that is, the out-side sensor is obtained by the following expression.

$$\text{Firmware\_position} = \text{Gain\_value} \neq (\text{encoder\_value} - \text{abs1}) \quad (3)$$

The in limit of the firmware position is appropriately set by the operator in a range where the table apparatus does not interfere with the PET-CT gantry.

After the characterization information and the configuration information with respect to all of the axes have been stored, a flag is set in Step S735. The flag expresses that the table apparatus identification has been completed. The flag setting in Step S735 is conducted by a computer within the operator console 400. The computer is an example of the flag setting means according to the present invention. With the setting of the flag, the presence or absence of the table apparatus identification can be clarified.

In Step S737, the configuration is displayed. The display is conducted by using the display 402. The configuration display is conducted by using a value that is calculated according to the configuration information.

Figure 12:
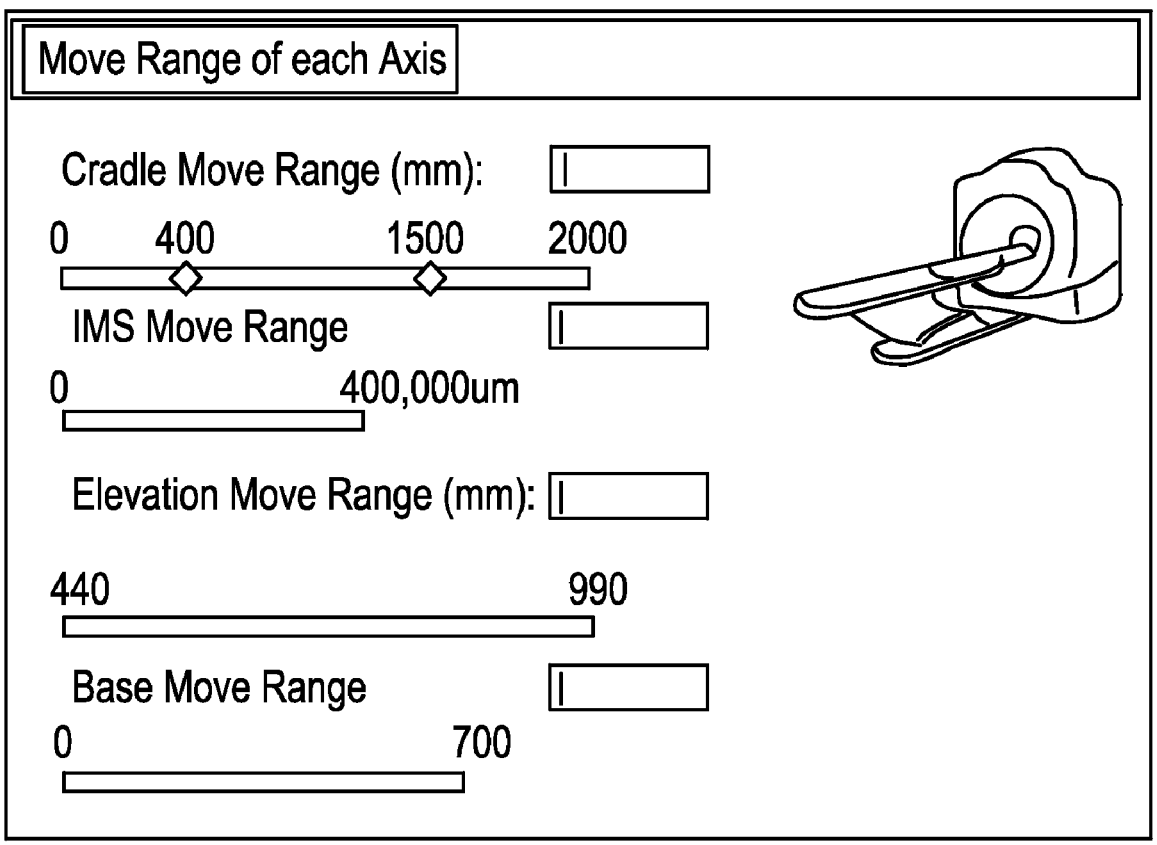
FIG. 12 is a diagram showing a user interface.

FIG. 12 shows an example of the user interface for configuration display. The user interface is an example of the user interface according to the present invention.

As shown in FIG. 12, a cradle movement range, an IMS movement range, an elevation movement range, and a transporter movement range are indicated by horizontal bars, respectively, in parallel with a perspective view of the table apparatus. The minimum value and the maximum value of the movement range are indicated at both ends of the respective bars by numerals. When the in limit is set in the movement range of the cradle by the operator, that value is also indicated. The values including the present position of the cradle and the in limit are indicated with different colors. In this way, the configuration of the table apparatus is displayed on the user interface, to thereby make it easy to confirm the configuration.

The configuration information can be supplied in response to a demand from a host device such as a host computer or TGP, or a user. The configuration information supply process is shown in FIG. 13.

Figure 13:
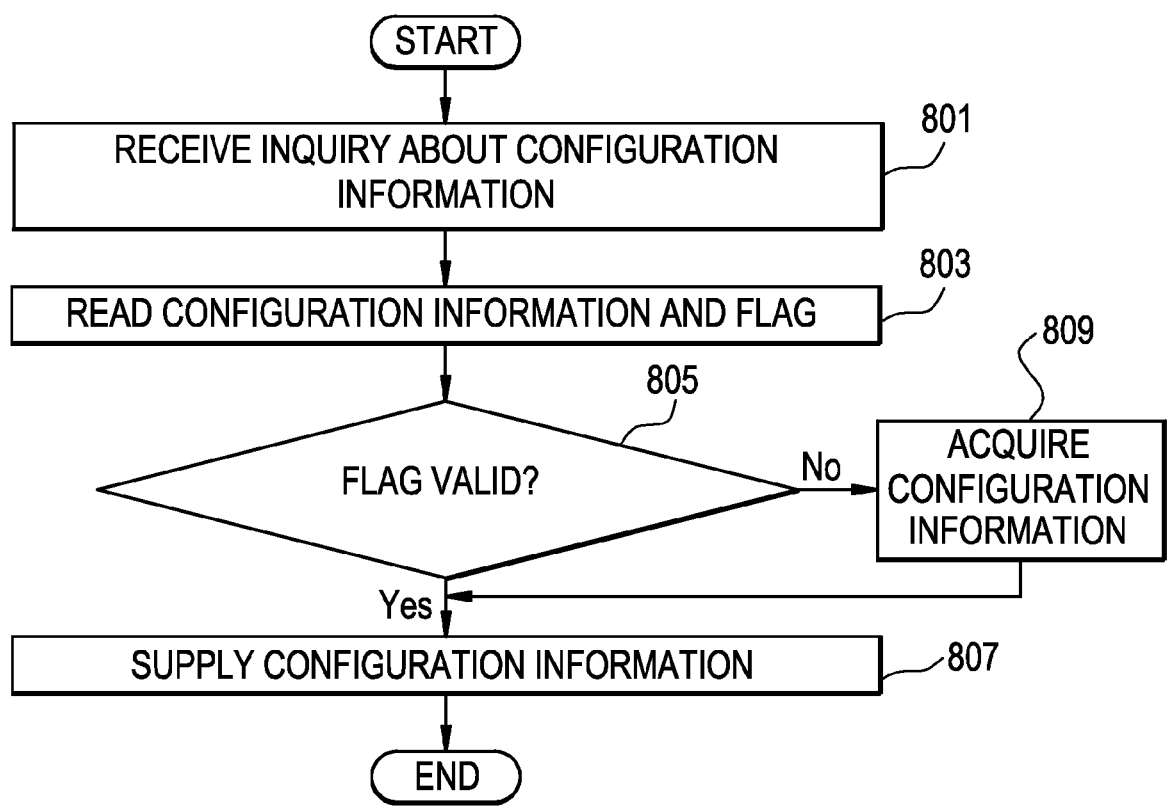
FIG. 13 is a flowchart showing a configuration information supply process.

As shown in FIG. 13, upon receiving an inquiry regarding the configuration information in Step S801, the configuration information and the flag are read out of the memory section in Step S803. Then, it is determined in Step S805 whether the flag is valid, or not. When the flag is valid, the configuration information is then supplied to the host device or the user in Step S807.

When it is determined that the flag is not valid, the configuration information is acquired in Step S809. The configuration information is acquired by the process shown in FIGS. 9 and 10. The acquired configuration information is supplied to the host device in Step S807.

The determination in Step S805 is conducted by a computer within the operator console 400. The computer is an example of determining means according to the present invention. In this way, since it is determined whether the table apparatus identification is required, or not, on the basis of the presence or absence of the flag, the duplex of the table apparatus identification can be prevented.

Many widely different embodiments of the invention may be configured without departing from the spirit and the scope of the present invention. It should be understood that the present invention is not limited to the specific embodiments described in the specification, except as defined in the appended claims.

The invention claimed is:

1. A method for identifying a table apparatus having at least a first axis and a second axis defined with respect thereto and including at least a first movable portion movable along the first axis and a second moveable portion movable along the second axis, the first movable portion and the second moveable portion independently movable with respect to each other, the method comprises for each axis:
    detecting absolute positions of a respective movable portion on the axis;
    optically detecting when the respective movable portion is positioned at one of a first predetermined position and a second predetermined position, the first predetermined position and the second predetermined position spaced apart from each other by a given distance along the axis.
    storing, as characterization information, a first absolute position of the respective movable portion when the respective movable portion is detected at the first predetermined position and a second absolute position of the respective movable portion when the respective movable portion is detected at the second predetermined position;
    detecting when the respective movable portion is positioned at one of a first block position at a first end of the axis and a second block position at a second end of the axis; and
    storing, as configuration information, a third absolute positions position of the respective movable portion when the respective movable portion is detected at the first block position and a fourth absolute position of the respective movable portion when the respective movable portion is detected at the second block position.

2. The method according to claim 1, further comprising positioning optical sensors at the first and second predetermined positions to detect when the respective movable portion is positioned at one of the first predetermined position and the second predetermined position.

3. The method according to claim 2 wherein positioning optical sensors comprises positioning light receiving sensors at the first and second predetermined positions.

4. The method according to claim 2, wherein positioning optical sensors comprises positioning light shielding sensors at the first and second predetermined positions.

5. The method according to claim 1, further comprising setting a flag after the characterization information and the configuration information are stored with respect to all of the axes.

6. The method according to claim 5, further comprising determining, based on a presence or an absence of the flag, whether the identification of the table apparatus is performed.

7. The method according to claim 1, the further comprising displaying a configuration of the table apparatus on an user interface based on the configuration information.

8. A medical imaging apparatus comprising:
    a first data collection unit configured to collect projection data attributable to radiation generated by a medicinal drug given to an object to be detected;
    a second data collection unit configured to scan the object with X-rays to collect the projection data;
    an image reconstruction unit configured to reconstruct images based on the projection data that has been collected by the first data collection unit and the second data collection unit;
    a table apparatus having at least a first axis and a second axis defined with respect thereto and comprising at least a first movable portion movable along the first axis and a second movable portion movable along the second axis, the first movable portion and the second movable portion movable independent of each other to selectively transport the object to at least one of a data collection position of the first data collection unit and a data collection position of the second data collection unit; and
    a table apparatus identifying unit that identifies the table apparatus, the table apparatus identifying unit comprising, for each movable portion:
        an absolute position detecting device configured to detect absolute positions of the movable portion on a respective axis;
        a first detecting device configured to optically detect when the movable portion is positioned at one of a first predetermined position and a second predetermined position, the first predetermined position and the second predetermined position spaced apart from each other by a given distance along the respective axis;
        a first memory device configured to store, as characterization information, a first absolute position of the movable portion when the first detecting device detects the movable portion at the first predetermined position and a second absolute position of the movable portion when the first detecting device detects the movable portion and the second predetermined position;

a second detecting device configured to detect when the movable portion is positioned at one of a first block position at a first end of the respective axis and a second block position at a second end of the respective axis; and second memory device configured to store, as configuration information, a third absolute position of the movable portion when the second detecting device detects the movable portion at the first block position and a fourth absolute position when the second detecting device detects the movable portion at the second block position.

9. The medical imaging apparatus according to claim 8, wherein the first detecting device comprises a first optical sensor positioned at the first predetermined position and a second optical sensor positioned at the second predetermined position.

10. The medical imaging apparatus according to claim 9, wherein the optical sensors comprise light receiving sensors.

11. The medical imaging apparatus according to claim 10, wherein the table apparatus identifying unit further comprises a flag setting device configured to set a flag after the characterization information and the configuration information are stored in the first memory device and the second memory device with respect to all of the axes.

12. The medical imaging apparatus according to claim 11, wherein the table apparatus identifying unit further comprises a determining device configured to determine whether to perform the identification of the table apparatus based on a presence or an absence of the flag.

13. The medical imaging apparatus according to claim 9, wherein the optical sensors comprise light shielding sensors.

14. The medical imaging apparatus according to claim 13, wherein the table apparatus identifying unit further comprises a flag setting device configured to set a flag after the characterization information and the configuration information are stored in the first memory device and the second memory device with respect to all of the axes.

15. The medical imaging apparatus according to claim 14, wherein the table apparatus identifying unit further comprises a determining device configured to determine whether to perform the identification of the table apparatus based on a presence or an absence of the flag.

16. The medical imaging apparatus according to claim 9, wherein the table apparatus identifying unit further comprises a flag setting device configured to set a flag after the characterization information and the configuration information are stored in the first memory device and the second memory device with respect to all of the axes.

17. The medical imaging apparatus according to claim 16, wherein the table apparatus identifying unit further comprises a determining device configured to determine whether to perform the identification of the table apparatus based on a presence or an absence of the flag.

18. The medical imaging apparatus according to claim 8, wherein the table apparatus identifying unit, further comprises a flag setting device configured to set a flag after the characterization information and the configuration information are stored in the first memory device and the second memory device with respect to all of the axes.

19. The medical imaging apparatus according to claim 18, wherein the table apparatus identifying unit further comprises a determining device configured to determine whether to perform the identification of the table apparatus based on a presence or an absence of the flag.

20. The medical imaging apparatus according to claim 8, wherein the table apparatus identifying unit further comprises a user interface configured to display a configuration of the table apparatus based on the configuration information.

\* \* \* \* \*